(12) United States Patent
Nemoto et al.

(10) Patent No.: US 8,445,413 B2
(45) Date of Patent: May 21, 2013

(54) LINKER FOR CONSTRUCTING MRNA-PUROMYCIN-PROTEIN CONJUGATE

(75) Inventors: Naota Nemoto, Saitama (JP); Manish Biyani, Saitama (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 603 days.

(21) Appl. No.: 11/665,300

(22) PCT Filed: Oct. 12, 2005

(86) PCT No.: PCT/JP2005/019163
§ 371 (c)(1),
(2), (4) Date: Oct. 30, 2007

(87) PCT Pub. No.: WO2006/041194
PCT Pub. Date: Apr. 20, 2006

(65) Prior Publication Data
US 2008/0312103 A1    Dec. 18, 2008

(30) Foreign Application Priority Data
Oct. 15, 2004 (JP) .................... 2004-301687

(51) Int. Cl.
*C40B 40/08* (2006.01)
*C40B 40/10* (2006.01)
*C07H 21/02* (2006.01)

(52) U.S. Cl.
USPC .................. 506/17; 536/23.1; 506/18

(58) Field of Classification Search
None
See application file for complete search history.

(56) References Cited

U.S. PATENT DOCUMENTS
2003/0100004 A1* 5/2003 Kurz .................. 435/6

FOREIGN PATENT DOCUMENTS
| EP | 1 211 514 A1 | 6/2002 |
| EP | 1 350 846 A1 | 10/2003 |
| JP | 2003-299489 A * | 10/2003 |
| JP | 2003-299489 A | 10/2003 |
| JP | 2004-097213 A | 4/2004 |
| WO | WO 01/07657 A1 | 2/2001 |
| WO | WO 2005/001086 A1 | 1/2005 |

OTHER PUBLICATIONS

Steyaert (1997 European Journal of Biochemistry vol. 247 p. 1).*
Steyaert (1997) European Journal of Biochemistry vol. 247 pp. 1 to 11.*
Sa-Ardyen (May 7, 2004) Journal of American Chemical Society vol. 126 pp. 6648 to 6657.*

(Continued)

*Primary Examiner* — Ardin Marschel
*Assistant Examiner* — Christian Boesen
(74) *Attorney, Agent, or Firm* — Foley & Lardner LLP

(57) ABSTRACT

The present invention provides a linker preferably used when constructing an mRNA/cDNA-puromycin-protein conjugate used in an in vitro virus method, and an mRNA/cDNA-puromycin-protein conjugate constructed using that linker. More specifically, the present invention provides a linker for ligating mRNA and puromycin or a puromycin-like compound to construct an mRNA/cDNA-puromycin-protein conjugate, the linker comprising a single-stranded RNA as a main backbone, and having, in this main backbone, a solid phase binding site for binding an mRNA-puromycin-protein conjugate to a solid phase site, and a pair of cleavage sites provided at locations surrounding the solid phase binding site; an mRNA-puromycin-protein conjugate constructed using this linker; an mRNA bead or an mRNA chip comprising this conjugate; a protein chip produced from this mRNA chip; and a diagnostic kit using the mRNA bead or the mRNA chip.

5 Claims, 3 Drawing Sheets

OTHER PUBLICATIONS

Chaput (2000) Journal of Molecular Evolution vol. 51 pp. 464 to 470.*

Miyamoto-Sato et al., "In vitro virus Oyobi Tanpakushitsu C Mallen Label-hako no Post Genome Kenkyu eno Oyo," Protein, nucleic acid and enzyme, 2003, vol. 48, No. 11, pp. 1474-1480.

Tabuchi et al., "An in vitro DNA virus for in vitro protein evolution," Federation of European Biochemical Societies, Letters, 2001, vol. 508, No. 3, pp. 309-312.

Biyani et al., "Solid-phase translation and RNA-protein fusion: a novel approach for folding quality control and direct immobilization of proteins using anchored mRNA," Nucleic Acids Research, 2006, 34(20)e140, 9 pgs.

Kurz et al., "cDNA-Protein Fusions: Covalent Protein- Gene Conjugates for the In Vitro Selection of Peptides and Proteins," ChemBioChem, Sep. 3, 2001, 2(9):666-672.

Nemoto et al., "In vitro virus: Bonding of mRNA bearing puromycin at the 3'-terminal end to the C-terminal end of its encoded protein on the ribosome in vitro," FEBS Letters, Sep. 8, 1997, 414(2):405-408.

Roberts et al. "RNA-peptide fusions for the in vitro selection of peptides and proteins," Proc. Natl. Acad. Sci. USA, Nov. 1, 1997, 94(23):12297-12302.

Tabuchi et al., "An Efficient Ligation Method in the Making of an in vitro Virus for in vitro Protein Evolution," Biol. Proced. Online, Oct. 28, 2002, 4(1):49-54.

Weng et al., "Generating addressable protein microarrays with PROfusion™ covalent mRNA-protein fusion technology," Proteomics, Jan. 1, 2002, 2(1):48-57.

* cited by examiner

SBP Linker     LBP Linker

SBP Linker     LBP Linker

LINKER FOR CONSTRUCTING MRNA-PUROMYCIN-PROTEIN CONJUGATE

TECHNICAL FIELD

The present invention relates to a linker for constructing an mRNA-puromycin conjugate or mRNA-puromycin-protein conjugate, and an mRNA-puromycin conjugate or mRNA-puromycin-protein conjugate constructed using that linker. In addition, the present invention relates to an mRNA bead or mRNA chip comprising the linker, a protein chip produced from this mRNA chip, and a diagnostic kit using the mRNA bead or the mRNA chip.

BACKGROUND ART

In the field of genome science, the emphasis has recently shifted from "structural analysis" involving the identification of gene sequences to "functional analysis" using gene expression products. This is because proteins and other gene products are basically provided with gene functions. For this reason, protein analysis is essential for analyzing the functions of genes. Analysis of protein function is carried through, for example, biochemical functional analyses by analyzing protein-protein interactions, protein-nucleic acid interactions and so on.

Known examples of methods for analyzing protein-protein interactions include the yeast two-hybrid method (Chien, C. T. et al., Proc. Natl. Acad. Sci. USA, 88, 9578-9582 (1991)), the phage display method (Smith, G. P., Science, 228, pp. 1315-1317 (1985)), the GST-fusion protein pull-down method, and the immunoprecipitation method or the like. Known examples of methods for analyzing protein-nucleic acid interactions include electrophoretic mobility shift assays (Revzin, A., et al., Anal. Biochem., 153, 172 (1986)), the DNase I footprint method (Calas, D., et al., Nucleic Acid Res., 5, 3157 (1978)) and the methylation buffer method.

In addition, methods for analyzing protein interactions are also being developed using an in vitro virus method (see Nemoto, et al., FEBS Lett., 414, 405 (1997); Tabuchi, et al., FEBS Lett., 508, 309 (2001)) utilizing specific properties of puromycin (see WO 01/016600).

The in vitro virus (IVV) method is a powerful protein evolutionary engineering technique involving the selection of a peptide that specifically bonds to a specific molecule (not limited to proteins) in a library of a vast number of peptides or proteins having random sequences. However, the high cost and inefficiency of "linkers" for ligating puromycin to mRNA is a major obstacle to practical use of this technique. It is important for practical linkers to satisfy conditions such as (1) good ligation efficiency between the linker and mRNA, (2) being able to be purified immediately from a translation system, having a reverse transcription DNA primer and being able to be rapidly converted to DNA, and (3) easy purification of converted DNA/RNA-protein conjugates. In order to efficiently proceed with the reverse transcription of (2) above in particular, it is important to translate using a biotin-labeled linker followed by promptly purifying the mRNA-protein conjugate from a cell-free translation system.

However, there is as of yet no known linker that simultaneously satisfies these three conditions, thus resulting in the need for the development of such a linker as well as mRNA/cDNA-puromycin-protein conjugates constructed using that linker.

DISCLOSURE OF THE INVENTION

In order to solve the above-mentioned problems of the prior art, the present invention provides a linker as described below, an mRNA-puromycin-protein conjugate constructed using that linker, an mRNA bead or mRNA chip comprising that linker, a protein chip produced from this mRNA, and a diagnostic kit using the mRNA bead or the mRNA chip.

(1) A linker for constructing an mRNA-puromycin conjugate, mRNA-puromycin-protein conjugate or mRNA/cDNA-puromycin-protein conjugate, comprising a single-stranded DNA, RNA and/or peptide nucleic acid (PNA) as a main backbone, and having, in the main backbone, a solid phase binding site for binding an mRNA-puromycin conjugate, mRNA-puromycin-protein conjugate or mRNA/cDNA-puromycin protein conjugate to a solid phase site, and a pair of cleavage sites provided at locations surrounding the solid phase binding site.

(2) The linker described in (1) above wherein the cleavage sites are enzyme cleavage sites.

(3) The linker described in (2) above wherein the enzyme cleavage sites are able to be cleaved by RNase T1, RNase A or RNase I.

(4) The linker described in (2) above wherein the enzyme cleavage sites are Ribo-G.

(5) The linker described in (2) above wherein the enzyme cleavage sites are pyrimidine nucleotides.

(6) The linker described in (2) above wherein the enzyme cleavage sites are RNA.

(7) The linker described in (1) above wherein the solid phase binding site is biotin-deoxythymine (deoxythymine bound with biotin), amino-modified deoxythymine, carboxy-modified deoxythymine or thiol-deoxythymine.

(8) The linker described in (7) above wherein the solid phase binding site is biotin-deoxythymine.

(9) The linker described in any of (1) to (8) above having a length of 10 to 60 mer.

(10) An mRNA-puromycin conjugate in which mRNA and puromycin or a puromycin-like compound are ligated with the linker described in any of (1) to (9) above.

(11) An immobilized mRNA-puromycin conjugate in which the mRNA-puromycin-protein conjugate described in (10) above is bound to a solid phase through a solid phase binding site provided in the linker described in any of (1) to (9) above.

(12) The immobilized mRNA-puromycin conjugate described in (9) above wherein the solid phase is selected from the group consisting of styrene beads, glass beads, agarose beads, sepharose beads, magnetic beads, glass plate, silicon plate, plastic plate, metal plate, glass container, plastic container and membrane.

(13) An mRNA chip comprising a plurality of the immobilized mRNA-puromycin conjugates described in (11) above.

(14) A protein chip produced using the mRNA chip described in (13) above.

(15) An mRNA bead obtained by immobilizing the immobilized mRNA-puromycin conjugate described in (11) above on a bead.

(16) A diagnostic kit comprising the mRNA chip described in (13) above or the mRNA bead described in (15) above and a cell-free translation system.

The linker of the present invention has the advantage of being able to be synthesized efficiently and produced inexpensively. In addition, since a linker in a preferred mode of the present invention can be designed to be shorter than a conventional linker, it also has the advantage of good ligation efficiency with mRNA. In addition, an mRNA-puromycin-protein conjugate constructed using the linker of the present invention has improved efficiency when removing the mRNA-puromycin-protein conjugate bound to a solid phase from the solid phase. Moreover, in the case of carrying out the in vitro virus method using an mRNA-puromycin-protein conjugate, there is also the advantage of being able to easily purify the resulting mRNA/cDNA-protein conjugate.

BEST MODE FOR CARRYING OUT THE INVENTION

Figure 1:
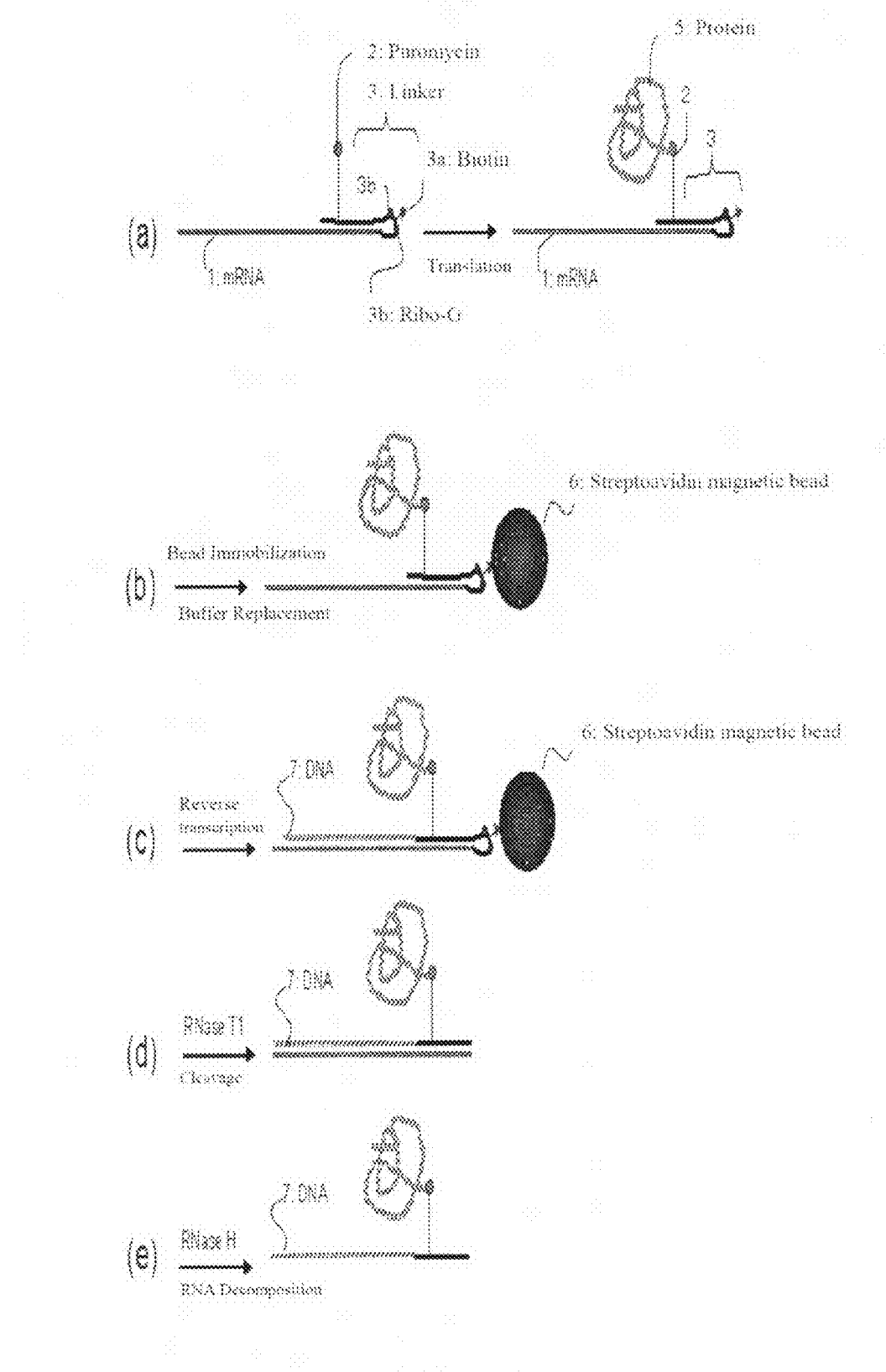
FIG. 1 is a drawing explaining the case of carrying out the in vitro virus method on an mRNA-puromycin-protein conjugate constructed using the linker of the present invention. In the drawing, 1 indicates mRNA, 2 puromycin, 3 the linker, 3a a solid phase binding site, 3b cleavage sites, 4 an mRNA-PM conjugate, 5 protein and 6 a streptoavidin magnetic bead.

The following provides a detailed explanation of the invention based on examples thereof.
1. Linker for Constructing mRNA-Puromycin-Protein Conjugate A first aspect of the present invention relates to a linker for ligating mRNA and puromycin or a puromycin-like compound to construct an mRNA-puromycin-protein conjugate. In the present invention, a "linker" refers to a linker for ligating mRNA and puromycin or a puromycin-like compound when constructing an mRNA-puromycin conjugate or mRNA-puromycin-protein conjugate used in the in vitro virus method. Here, an mRNA-puromycin conjugate is referred to as an "mRNA-PM conjugate", an mRNA-puromycin-protein conjugate is referred to as an "mRNA-PM-PRT conjugate", while an mRNA-PM conjugate or mRNA-PM-PRT conjugate is referred to as an "mRNA-PM-(PRT) conjugate". This linker is primarily inserted between mRNA and puromycin to allow the puromycin to be efficiently taken up at a site referred to as the A site of a ribosome. In addition, by providing a solid phase binding site in this linker, mRNA-PM-(PRT) can be bound to a solid phase, making it possible to efficiently carry out various reactions.

The linker of the present invention comprises a single-stranded DNA and/or a peptide nucleic acid as the main backbone thereof, and has a solid phase binding site for binding the mRNA-PM-(PRT) to the binding site, and a pair of cleavage sites provided at locations surrounding the solid phase binding site (locations at which the solid phase binding site is placed between the cleavage sites), in this main backbone. Furthermore, differing from DNA and RNA, a peptide nucleic acid (PNA) is a compound having a structure resembling DNA that forms a backbone with peptide bonds instead of phosphate bonds. The linker of the present invention is generally designed to have a flexible, hydrophilic backbone having a simple structure with few side chains. The linker of the present invention comprises single-stranded DNA and/or PNA as the backbone thereof, and can have a backbone portion other than the single-stranded DNA and/or PNA backbone portion provided the function of the linker as described above is fulfilled. An linear substance such as an RNA chain, polyalkylene such as polyethylene, polyalkylene glycol such as polyethylene glycol or combination thereof, for example, can be selected for the portion in the linker of the present invention other than the single-stranded DNA and/or PNA. When using these linear substances in combination, they can be chemically ligated with a suitable linking group (such as —NH—, —CO—, —O—, —NHCO—, —CONH—, —NHNH—, —(CH$_2$)$_n$— (wherein, n is, for example, 1 to 10 and preferably 1 to 3), —S— or —SO—). Furthermore, in the present description, "comprising single-stranded DNA and/or PNA as the main backbone thereof" refers to, for example, 60% or more, preferably 70% or more, more preferably 80% or more and most preferably 90% or more of the total length of the linker backbone being composed of single-stranded DNA and/or PNA. Furthermore, in the case of containing both DNA and PNA in the main backbone, although there are no particular limitations on the ratio thereof, the ratio of DNA:PNA is, for example, within the range of 1:9 to 9:1.

The linker of the present invention has a solid phase binding site for binding an mRNA-PM-(PRT) conjugate to a solid phase in the main backbone thereof. This solid phase binding site is a site for binding, for example, an mRNA-PM-(PRT) conjugate to a solid phase, examples of which include nucleotides capable of binding a compound or linkage group that binds an mRNA-PM-(PRT) conjugate to a solid phase, or a nucleotide bound with a compound or linkage group that binds an mRNA-PM-(PRT) conjugate to a solid phase. More specifically, examples of the solid phase binding site include a nucleotide capable of binding biotin (such as deoxythymine (dT)) or a nucleotide bound with biotin (such as biotin-deoxythymine (Biotin-dT)), a nucleotide modified by an amino group (such as amino-modified deoxythymine (for example, Amino-Modifier C6-dT: Glen Research Search)), a nucleotide modified by a carboxy group (such as carboxy-modified deoxythymine (Carboxy-dT)), and a nucleotide modified by a thiol group (such as thiol-modified deoxythymine (4-Thio-dT)). In a preferable aspect of the present invention, the solid phase binding site is biotin-deoxythymine. An mRNA-PM-(PRT) conjugate ligated with biotin can be bound to a solid phase on which avidin is immobilized through this solid phase binding site by utilizing the affinity between biotin and avidin. Furthermore, in the case a nucleotide bound with a carboxyl group or amino group has been selected for the solid phase binding site, the solid phase and the mRNA-PM-(PRT) conjugate can be bound with ester bonds or amide bonds.

The linker of the present invention is provided with a pair of cleavage sites at locations surrounding the solid phase binding site to remove the mRNA-PM-(PRT) conjugate from the solid phase as necessary. There are no particular limitations on these cleavage sites, and can be, for example, enzyme cleavage sites. In a preferable aspect of the present invention, the cleavage sites are enzyme cleavage sites such as Ribo-G (guanosine). When removing an mRNA-PM-(PRT) conjugate bound to a solid phase from the solid phase, the cleavage sites are cleaved with an enzyme and so on. Examples of enzymes that can be used here include RNase T1, RNase A, RNase I, pancreatic RNase, S1 nuclease, snake venom nuclease, splenic phosphodiesterase, *staphylococcus* nuclease, mung bean nuclease and red bread mold nuclease. In the present invention, RNase T1, RNase A, RNase I and pancreatic RNase are preferable, while RNase T1 is particularly preferable. The enzyme cleavage sites can be suitably selected according to the type of enzyme used.

The linker of the present invention preferably has a length of 10 to 60 mer, more preferably 10 to 45 mer, and even more preferably 15 to 30 mer, in consideration of such factors as the reactivities of the various reaction steps and the purification efficiency of the resulting DNA/protein conjugate. Furthermore, the linker of the present invention can be produced using known chemical synthesis techniques.

2. Immobilized mRNA-Puromycin Conjugate

The present invention also relates to an mRNA-PM conjugate comprising the ligation of mRNA and puromycin using the linker described above.

The mRNA used in the present invention includes that having an unknown sequence and that having a known sequence. Namely, in the case of searching for or quantifying a substance that binds with a protein having a known sequence using the mRNA-PM conjugate of the present invention, mRNA having a nucleic acid sequence that encodes a protein having a known sequence is used. Conversely, in the case of analyzing the function of a protein having an unknown sequence using the mRNA-PM conjugate of the present invention, mRNA having a nucleic acid sequence that encodes a protein having an unknown sequence can be used. The mRNA used here is selected from, for example, mRNA encoding various types of receptor proteins having a known sequence, mRNA encoding various antibodies or fragments thereof, mRNA encoding various enzymes, mRNA having an unknown sequence transcribed from DNA in various gene libraries, or mRNA having a random sequence transcribed from DNA having a sequence randomly synthesized by organic synthesis.

The mRNA-PM conjugate of the present invention is normally ligated with puromycin (PM) through the above-mentioned linker at the 3' terminal of mRNA. Here, the puromycin or puromycin-like compound fulfills the role of a hinge or coupling that ligates mRNA and a translated protein when synthesizing a protein by adding the mRNA-PM conjugate immobilized on a solid phase to a translation system. Namely, when a conjugate in which puromycin is ligated to mRNA through the linker is contacted with a translation system, an in vitro virus virion is known to be formed in which the mRNA is ligated with a translated protein through the puromycin (see Nemoto, et al., FEBS Lett., 414, 405 (1997)). Puromycin is a compound represented by the following formula (I):

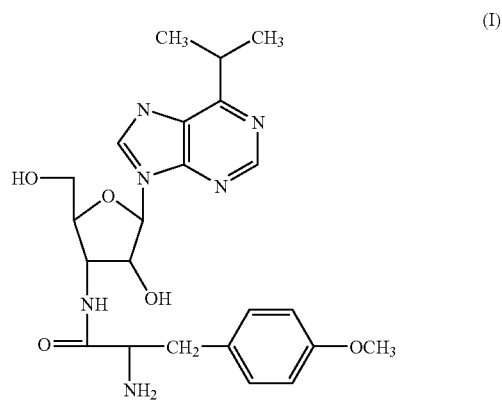

in which the 3' terminal has a chemical structural backbone that resembles aminoacyl tRNA, and when protein synthesis has been carried out in a translation system, has the ability to bind to the C terminal of the synthesized protein. In the present description, a "puromycin-like compound" refers to a compound in which the chemical structural backbone of the 3' terminal resembles aminoacyl tRNA, and has the ability to bind to the C terminal of a synthesized protein when protein synthesis has been carried out in a translation system.

Examples of puromycin-like compounds include 3'-N-aminoacylpuromycin aminonucleotides (PANS-amino acids), and more specifically, PANS-Gly in which the amino acid portion is glycine, PANS-Val in which the amino acid portion is valine, PANS-Ala in which the amino acid portion is alanine, and other PANS-amino acid compounds corresponding in which the amino acid portions correspond to any amino acid. In addition, 3'-N-aminoacyladenosine aminonucleotides (AANS-amino acids), which are formed by dehydration and bonding of an amino group of 3'-aminoadenosine and a carboxyl group of the amino acid, examples of which include AANS-Gly in which the amino acid portion is glycine, AANS-Val in which the amino acid portion is valine, AANS-Ala in which the amino acid portion is alanine, and other AANS-amino acid compounds, in which the amino acid portions correspond to any amino acid, can also be used. In addition, nucleosides or ester bound forms of nucleosides and amino acids can also be used. Furthermore, examples of puromycin-like compounds used preferably in addition to the puromycins described above include ribositidyl puromycin (rCpPur), deoxydyl puromycin (dCpPur) and deoxyuridyl puromycin (dUpPur), and are represented by the chemical structural formulas shown below.

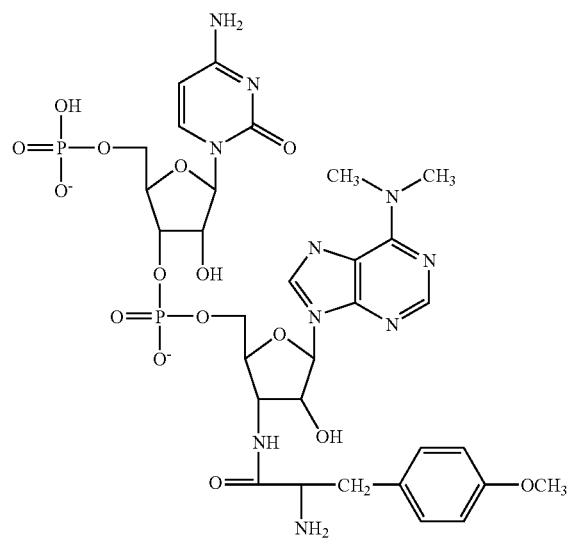
rCpPur
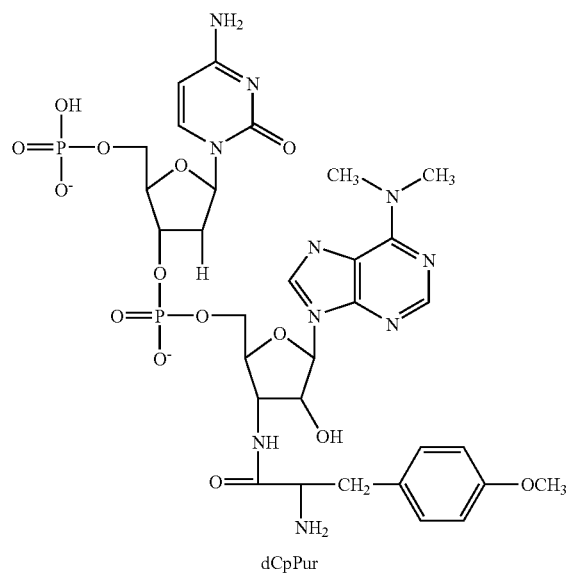
dCpPur
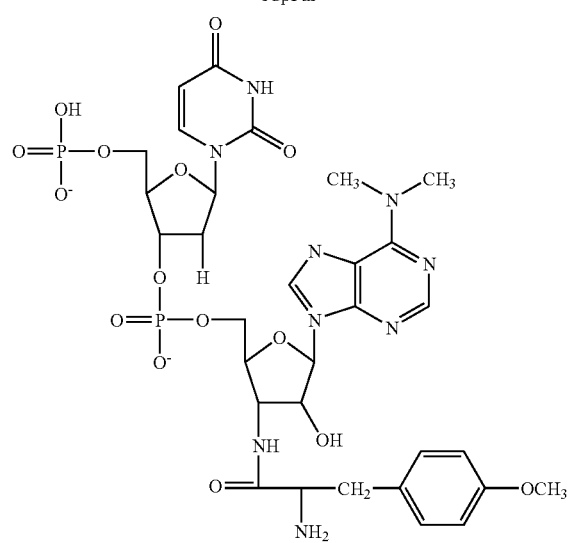
dUpPur
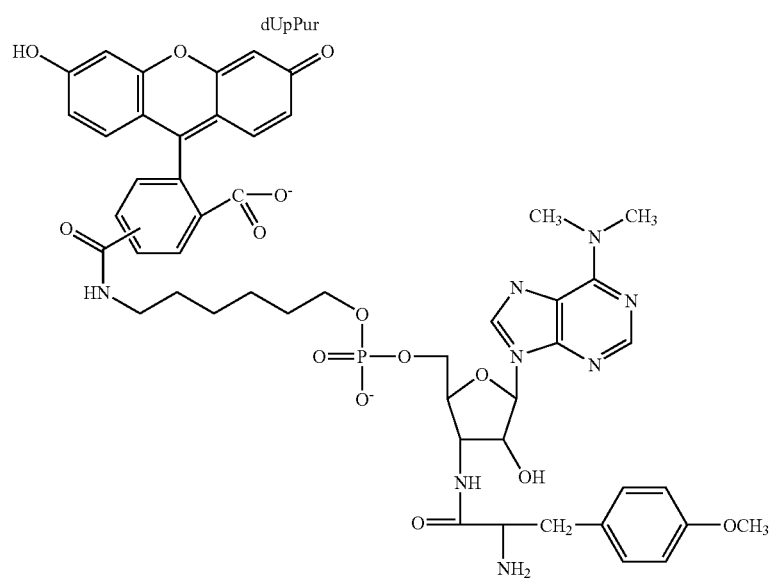
Fluoropur

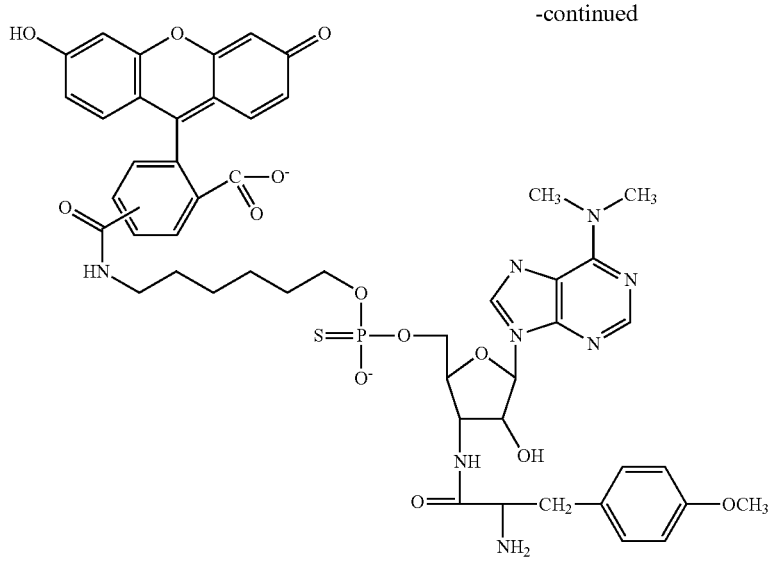

Lurothiopur

Ligation of mRNA and the linker can be carried out directly or indirectly, and chemically or physically using a known technique. For example, in the case of using DNA as a linker, by providing a sequence complementary to a terminal of the linker DNA on the 3' terminal of the mRNA, the two can be ligated. In addition, in the case of ligating the linker and puromycin, the two are normally ligated by a known chemical technique.

In addition, when constructing an mRNA-PM conjugate, an mRNA-PM conjugate can be constructed by forming a portion of the linker on the 3' terminal side of the mRNA when preparing the mRNA, and then binding the remainder of the linker ligated to puromycin thereto. In this case, a cleavage site can also be provided in the portion of the linker formed on the 3' terminal side of the mRNA.

Furthermore, the mRNA-PM conjugate of the present invention can be labeled by binding a label as necessary. A fluorescent substance or radioactive substance and so on is suitably selected for such a label. Various fluorescent pigments having a free functional group (such as a carboxyl group capable of being converted to an active ester, a hydroxyl group capable of being converted to a phosphoramidite, or an amino group), and able to be ligated to a linker, puromycin or a puromycin-like compound can be used for the fluorescent substance. Examples of suitable labels include fluorescent substances such as fluorescein isothiocyanate, phycobiliprotein, rare earth metal chelates, dansyl chloride or tetramethyl rhodamine isothiocyanate; and, radioisotopes such as $^3$H, $^{14}$C, $^{125}$I or $^{131}$I.

3. Immobilized mRNA-PM Conjugate

According to a different aspect of the present invention, an immobilized mRNA-PM conjugate is provided obtained by immobilization of the mRNA-PM conjugate on a solid phase through the solid phase binding site of the linker.

There are no particular limitations on the solid phase on which the mRNA-PM conjugated is immobilized, and is suitably selected corresponding to the purpose for which the conjugate is used. A carrier that immobilizes biomolecules can be used for the solid phase used in the present invention, examples of which include beads such as styrene beads, glass beads, agarose beads, sepharose beads or magnetic beads; plates such as glass plates, silicon (quartz) plates, plastic plates or metal plates (such as gold foil plates); containers such as glass containers or plastic containers; and membranes made from materials such as nitrocellulose or polyvinylidene fluoride (PVDF). Furthermore, in the present description, beads on which the mRNA-PM conjugate is immobilized are referred to as "mRNA beads".

In the mRNA-PM conjugate of the present invention, a solid phase binding site is provided for the linker that ligates the mRNA and PM, and that solid phase binding site immobilizes the mRNA-PM conjugate on the solid phase through a "solid phase binding site recognition site" bound to the solid phase. There are no particular limitations on the solid phase binding site provided it is able to bind the mRNA-PM conjugate to a desired solid phase. For example, a molecule (such as a ligand or antibody) that specifically binds to a specific polypeptide is used as such a solid phase binding site, and in this case, the specific polypeptide that binds with that molecule is bound to the surface of the solid phase in the form of a solid phase binding site recognition site. Examples of combinations of solid phase binding sites and solid phase binding site recognition sites include biotin-binding proteins, such as avidin and streptoavidin, and biotin, maltose-binding proteins and maltose, G proteins and guanine nucleotides, polyhistidine peptides and metal ions such as nickel or cobalt ions, glutathione-S-transferase and glutathione, DNA-binding proteins and DNA, antibodies and antigen molecules (epitopes), calmodulin and calmodulin-binding peptides, ATP-binding proteins and ATP and various types of receptor proteins and their ligands such as estradiol receptor protein and estradiol.

Preferable examples of these combinations of solid phase binding sites and solid phase binding site recognition sites include biotin-binding proteins, such as avidin and streptoavidin, and biotin, maltose-binding proteins and maltose, polyhistidine peptides and metal ions such as nickel or cobalt ions, glutathione-S-transferase and glutathione, and antibodies and antigen molecules (epitopes), with the combination of streptoavidin and biotin being the most preferable.

A known method can be used to bind the above-mentioned proteins to the surface of a solid phase. Examples of such known methods include methods using tannic acid, formalin, glutaraldehyde, pyruvic aldehyde, bis-diazotized benzizone, toluene-2,4-diisocyanate, amino groups, carboxyl groups, hydroxyl groups or amino groups (see P. M. Abdella, P. K. Smith, G. P. Royer: A New Cleavable Reagent for Cross-Linking and Reversible Immobilization of Proteins, Biochem. Biophys. Res. Commun., 87, 734 (1979)).

Furthermore, the above-mentioned combinations can also be used by reversing the solid phase binding site and solid phase binding site recognition site. Although the immobilization means is an immobilization method that uses a substance having mutual affinity for both, if the solid phase is a styrene bead, styrene plate or other plastic material, a portion of the linker can also be covalently bonded to the solid phase using a known technique (see Qiagen Corp., LiquiChip Applications Handbook). Furthermore, in the present invention, the immobilization means is not limited to the methods described above, but rather any immobilization means known among persons with ordinary skill in the art can also be used.

4. Protein Solid Phase Immobilization Method and Protein Solid Phase Synthesis Method According to another aspect of the present invention, a protein solid phase immobilization or solid phase synthesis method is provided comprising the steps of: (a) preparing an mRNA-PM conjugate by ligating mRNA and puromycin through the above-mentioned linker, (b) immobilizing the mRNA-PM conjugate on a solid phase by ligating a solid phase binding site of the linker to a solid phase, and (c) synthesizing a protein by contacting the mRNA-PM conjugate with a translation system (by, for example, adding a translation system to the conjugate or adding the conjugate to a translation system). In step (b), since an mRNA-PM conjugate is immobilized on a solid phase, the synthesized protein is immobilized on the solid phase through the puromycin using corresponding technology of the previously described in vitro virus method when this conjugate is added to a translation system.

In step (c) above, protein synthesis is carried out by contacting the mRNA-PM conjugate with a translation system. Examples of translation systems able to be used here include cell-free translation systems and viable cells. Examples of cell-free translation systems include cell-free translation systems composed of extracts of prokaryotic or eukaryotic organisms, such as *Escherichia coli*, rabbit reticulocyte or wheat germ extracts (see Lamfrom, H, Grunberg-Managо, M.: Ambiguities of translation of poly U in the rabbit reticulocyte system, Biochem. Biophys. Res. Commun., 1967, 27(1): 1-6). Examples of viable cell translation systems that can be used include prokaryotic or eukaryotic cells such as cells of *Escherichia coli*. In the present invention, a cell-free system is used preferably in consideration of handling ease.

The following provides a brief explanation of the process of the in vitro virus method using the mRNA-PM conjugate of the present invention based on FIG. 1.

In FIG. 1(a), reference symbol 1 indicates mRNA, 2 puromycin, and both compose an mRNA-PM conjugate 4 as a result of being ligated through a linker 3. The linker 3 has a solid phase binding site 3a and cleavage sites 3b. Furthermore, reference symbol 5 indicates a protein bound to the puromycin 2. In FIGS. 1(b) and 1(c), reference symbol 6 indicates a streptoavidin magnetic bead bound to the solid phase binding site 3a. In FIGS. 1(c) and 1(d), reference symbol 7 indicates DNA formed by reverse transcription. Furthermore, in FIGS. 1(b) to 1(e), duplicate reference symbols are omitted.

In the in vitro virus method, first, as shown in FIG. 1(a), a protein corresponding to the mRNA is synthesized by applying the mRNA-PM conjugate 4 to a translation system such as a cell-free translation system. This protein is bound to the puromycin 2 as shown in the drawing. Next, the resulting mRNA-PM-PRT conjugate is immobilized on the bead 6 (FIG. 1(b)), and by applying this to a reverse transcription reaction, DNA corresponding to the mRNA is formed (FIG. 1(c)). Here, if the linker is cleaved at cleavage sites 3b by an enzyme such as RNase TI, the streptoavidin magnetic bead 6 can be removed (FIG. 1(d)). Moreover, a DNA-protein conjugate, in which protein and DNA that encodes that protein are ligated, is formed by degrading the mRNA with RNase H as necessary. Protein functions and so on can then be efficiently analyzed by applying the mRNA/cDNA-PM-PRT conjugate (complex) or DNA-protein conjugate (complex) obtained in this manner to various analytical experiments.

5. mRNA Chip and Protein Chip

According to another aspect of the present invention, an mRNA chip (mRNA microarray) is provided that contains a plurality of the above-mentioned immobilized mRNA-PM conjugates. This mRNA chip has a plurality of the mRNA-PM conjugates described above immobilized on a plate. The protein synthesis described above takes place on the chip and a so-called protein chip, in which each protein is bound to a solid phase, can be produced by adding this mRNA chip to a translation system or adding a translation system to the mRNA chip.

In the mRNA chip of the present invention, a plurality of mRNA encoding proteins having known functions may be immobilized on a solid phase as mRNA-PM conjugates, or a plurality of mRNA encoding proteins having unknown functions may be immobilized on a solid phase as mRNA-PM conjugates. For example, an mRNA chip for diagnosing diseases can be obtained in the case of immobilizing a plurality of mRNA encoding proteins having known functions involved in diseases on a chip. In this case, mRNA encoding proteins that bind with diagnostic markers of specific diseases are respectively immobilized at predetermined locations on a plate. A cell-free translation system is then added to the plate immediately before carrying out diagnosis, and the protein that binds with a desired diagnostic marker at a predetermined location on the plate is synthesized and immobilized. When done in this manner, a protein chip can be produced immediately prior to diagnosis. Protein chips have problems with respect to storage and handling. The present invention enables a chip to be obtained in the form of stable mRNA instead of protein. For this reason, known protein chip technologies (for example, the material and size of the plate used, type and sequence of the protein used, and methods for analyzing the functions of proteins used in a protein chip) are able to be used for technologies other than the technologies for mRNA solid phase immobilization and protein synthesis and immobilization (see Kukar, T., Eckenrode, S., Gu, Y., Lian, W., Megginson, M., She, J. X., Wu, D.: Protein microarrays to detect protein-protein interactions using red and green fluorescent proteins, Anal. Biochem., 2002; 306(1): 50-4). Furthermore, a diagnostic kit comprising the above-mentioned mRNA beads or mRNA chip and a cell-free translation system is also included in the scope of the present invention. This type of mRNA chip can be used to evaluate protein-protein interactions, DNA-protein interactions, search for ligands, search for disease markers, diagnose diseases, evaluate pharmacological efficacy or evaluate pharmacodynamics and so on.

6. Method for Analyzing Interactions Between Proteins and Molecules

According to another aspect of the present invention, a method for analyzing interactions between proteins and molecules is provided that uses the previously described mRNA-PM conjugate. This analytical method comprises the steps of:

(a) adding one or more immobilized mRNA-PM conjugates to a translation system to synthesize protein on a solid phase, (b) contacting the protein synthesized in step (a) with one or more target substances, and (c) measuring whether or not there is interaction between the protein and the target substance.

This analytical method can be used in the case of, for example, (i) screening for a substance that acts on a protein having a known sequence, or (ii) screening for a protein having an unknown sequence that is bound by a certain specific substance (such as a ligand). In the case of (i), for example, a plurality of conjugates of mRNA having nucleic acid sequences that encode proteins having known sequences (such as an orphan receptor proteins) and puromycin are prepared (namely, a plurality of mRNA-PM conjugates each having mRNA corresponding to a plurality of orphan receptor proteins) followed by the addition thereof to a translation system. Whereupon, a plurality of orphan receptor proteins are synthesized from the mRNA of each mRNA-PM conjugate. Each orphan receptor protein is immobilized as a result of the C terminal binding to the puromycin of the mRNA-PM conjugates immobilized on a solid phase. A binding experiment is then carried out by then washing and removing unnecessary components as necessary, adding a target substance, buffer and so on thereto and binding the target substance to the orphan receptor protein. In the case of (ii), a plurality of mRNA are acquired from, for example, a certain gene library, conjugates are constructed of the plurality of mRNA and puromycin, and the resulting conjugates are immobilized on a solid phase. Protein synthesis is then carried out in the same manner and a binding experiment is conducted by contacting a target substance with that protein.

In the above-mentioned step (b), the protein synthesized in step (a) is contacted with one or more target substances. A "target substance" used here refers to a substance for investigating whether or not there is interaction with a protein synthesized in the present invention, specific examples of which include proteins, nucleic acids, sugar chains and low molecular weight compounds.

There are no particular limitations on the protein, and the protein may be a full-length protein or a partial peptide comprising an active binding site. In addition, the protein may be a protein having a known amino acid sequence and known function or a protein for which they are unknown. These can be used as target molecules in the form of synthesized peptide chains, proteins purified from the body, or proteins translated and purified using a suitable translation system from a cDNA library. Synthesized peptide chains may also be glycoproteins having a sugar chain bound thereto. These are preferably purified proteins having a known amino acid sequence, or proteins translated and purified using a suitable method from a cDNA library and the like.

There are no particular limitations on the nucleic acid, and DNA or RNA can be used. In addition, the nucleic acid may be that having a known nucleotide sequence or function or that for which the nucleotide sequence and function are unknown. A nucleic acid having the ability to bind to protein and having a known function and nucleotide sequence, or a nucleic acid isolated by cleaving from a genome library and the like using a restrictase and so on can be used preferably.

There are no particular limitations on the sugar chain, and may be a sugar chain having a sugar sequence and function that are known or unknown. A sugar chain for which the sugar sequence or function are known as a result of being previously separated and analyzed is used preferably.

There are no particular limitations on the low molecular weight compound, and that for which the function thereof is unknown, or that for which the ability to bind to protein is already known can be used.

Furthermore, although the "interaction" between the target substance and the protein normally demonstrates an action attributable to a force acting between molecules resulting from at least one of a covalent bond, hydrophobic bond, Van der Waals bond and a bond resulting from electrostatic force between the protein and the target substance, this term is to be interpreted in the broad sense, and is not to be considered to be a limiting interpretation in any sense. Covalent bonds include coordinate bonds and bipolar bonds. In addition, bonds resulting from electrostatic force include electrostatic bonds as well as electrical repulsion. In addition, bonding reactions, synthesis reactions and decomposition reactions occurring as a result of the above-mentioned action are also included in interactions. Specific examples of interactions include binding and dissociation between an antigen and antibody, binding and dissociation between a protein receptor and a ligand, binding and dissociation between an adhesion molecule and a corresponding molecule, binding and dissociation between an enzyme and a substrate, binding and dissociation between a nucleic acid and a protein binding thereto, and binding and dissociation between corresponding proteins in an information transmission system, binding and dissociation between a glycoprotein and a protein, and binding and dissociation between a sugar chain and a protein.

The target substance used here can be used after labeling with a label as necessary. The target substance can be labeled by binding a label as necessary. Such labels are suitably selected from fluorescent substances, radioactive labels and so on. Various fluorescent pigments having a free functional group (such as a carboxyl group capable of being converted to an active ester, a hydroxyl group capable of being converted to phosphoramidite, or amino group) and capable of being ligated to the target substance can be used as a fluorescent substance. Examples of suitable labels include fluorescein isothiocyanate, phycobiliprotein, rare earth metal chelates, dansyl chloride or tetramethyl rhodamine isothiocyanate; and, radioisotopes such as $^3$H, $^{14}$C, $^{125}$I or $^{131}$I. These labels are suitable for methods for measuring or analyzing changes in a signal generated based on an interaction between the target substance and an immobilized protein. Binding of the target substance to the label can be carried out based on known techniques.

Next, according to the present analytical method, in step (c), whether or not the protein and the target substance interact is measured. Measurement as to whether the protein and the target substance interact is carried out by measuring and detecting a change in a signal generated based on interaction between both molecules. Examples of such measurement methods include a surface plasmon resonance method (Cullen, D. C. et al., Biosensors, 3(4), 211-225 (1987-88), an evanescent field molecular imaging method (Funatsu, T., et al., Nature, 374, 555-559 (1995)), a fluorescent imaging analysis method, an enzyme-linked immunosorbent assay (ELISA) method (Crowther, J. R., Methods in Molecular Biology, 42 (1995)), a fluorescent polarization extinction method (Perran, J., et al., J. Phys. Rad., 1, 390-401 (1926)) and a fluorescent correlation spectroscopy (FCS) method (Eigen, M., et al., Proc. Natl. Acad. Sci. USA, 91, 5740-5747 (1994)).

In the analytical method of the present invention, the protein and/or the target substance in the protein-target substance conjugate for which there has been judged to be interaction in step (c) are identified as necessary. Identification of the protein can be carried out with an ordinary amino acid sequencer, or by reverse transcription of DNA from the mRNA bound to the protein followed by analysis of the nucleotide sequence of the resulting DNA. Identification of the target substance can be carried out by various types of mass analysis such as NMR and IR. In the case of analyzing the interaction between a protein and a target substance using the mRNA chip and protein chip of the present invention, analysis can be carried out using a time-of-flight type of mass spectrometer (MALDI-TOF MS) in the same manner as analysis of a sample on an ordinary protein chip.

EXAMPLES

The following provides a more detailed explanation of the present invention with reference to working examples thereof. However, the present invention is not limited to these examples.

Example

Synthesis of In Vitro Virus Virion (RNA/DNA-Protein Conjugate) Using a Novel Linker (1) Comparison of Synthesis Efficiency Between Novel Linker and Conventional Linker 1. In Vitro Virus Linker: Synthesis of Short-Biotin-Puromycin Linker (SBP Linker) and Long-Biotin-Puromycin Linker (LBP Linker)

First, the specially synthesized DNA was purchased from BEX.
(A) Puro-F-S [Sequence: 5'-(S)-TC(F)-(Spacer 18)-(Spacer 18)-(Spacer 18)-(Spacer 18)-CC-(Puro)-3']

Here, (S) indicates 5'-Thiol-Modifier C6, (Puro) indicates puromycin CPG, (Spacer 18) indicates a spacer having the trade name of "Spacer Phosphoramidite 18", having the chemical name (18-0-dimethoxytritylhexaethyleneglycol, 1-[(2-cyanoethyl)-(N,N-diisopropyl)]-phosphoramidite), and having the chemical structure indicated below (all available from Glen Research Search).

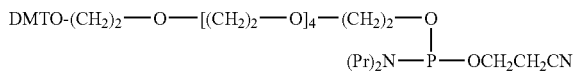

(B) Hybri [SEQ ID NO. 1: 5'-CC(rG)C(T-B) C(rG)CCC CGCCG CCCCC CG(T)CC T-3']

Here, (rG) indicates Ribo-G, (T) indicates Amino-Modifier C6 dT (5'-dimethoxytrityl-5-[N-(trifluoroacetylaminohexyl)-3-acrylimido]-2'-deoxyuridine, 3'-[(2-cyanoethyl)-(N,N-diisopropyl)]-phosphoramidite), and (T-B) indicates Biotin-dT (5'-dimethoxytrityloxy-5-[N-(((4-t-butylbenzoyl)-biotinyl)-aminohexyl)-3-acrylimido]-2'-deoxyuridine-3'-[(2-cyanoethyl)-(N,N-diisopropyl)]-phosphoramidite) (all available from Glen Research Search).
(C) Biotin-loop [(56 mer) SEQ ID NO. 2: 5'-CCCGG TG CAG CTGTT TCATC (T-B) CGGAAACAG CTGCA CCCCC CGCCG CCCCC CG(T)CCT-3'] (Underlines indicate restrictase PvuII sites.)

The linker of the present invention was purified by crosslinking (A) Puro-F-S and (B) Hybri according to the method described below. This was named "SBP linker". In addition, an "LBP linker" was synthesized by crosslinking (A) Puro-F-S and (B) Biotin-loop for comparison purposes. The following provides a description of the synthesis method.

Ten (10) nmol of Puro-F-S were dissolved in 100 µl of 50 mM phosphate buffer (pH 7.0) followed by the addition of 1 µl of 100 mM Tris-[2-carboxyethyl]phosphine (TECP, Pierce) (final concentration: 1 mM), allowing to stand for 6 hours at room temperature to reduce the Thiol of the Puro-F-S. Immediately before carrying out the crosslinking reaction, the TCEP was removed using NAP5 (Amersham, 17-0853-02) equilibrated with 50 mM phosphate buffer (pH 7.0).

Twenty (20) µl of 500 pmol/µl Hybri or Biotin-loop and 20 µl of 100 mM crosslinking agent EMCS (344-05051, 6-maleimidohexanoic acid N-hydroxysuccinide ester, Dojindo) were added to 100 µl of 0.2 M phosphate buffer (pH 7.0) and stirred well followed by allowing to stand for 30 minutes at 37° C. and removing the unreacted EMCS. After drying the precipitate under reduced pressure, the dried precipitate was dissolved in 10 µl of 0.2 M phosphate buffer (pH 7.0) followed by addition of the above-mentioned reduced Puro-F-S (up to 10 nmol) and allowing to stand overnight at 4° C. After adding TCEP to the sample to a final concentration of 4 mM and allowing to stand for 15 minutes at room temperature, the unreacted Puro-F-S was removed by ethanol precipitation, and HPLC purification was carried out under the following conditions to remove the unreacted Hybri or Biotin-loop.

Column: Nacalai Tesque CSOMOSIL 37918-31, 10×250 mm C18-AR-300 (Waters)

Buffer A: 0.1 M TEAA, Buffer B: 80% acetonitrile (diluted with ultrapure water)

Flow rate: 0.5 ml/min (B %: 15 to 35%, 33 min)

The HPLC fractions were analyzed with 18% acrylamide gel (8 M urea, 62° C.), and after drying the target fraction under reduced pressure, the dried fraction was dissolved with DEPC treatment water to a concentration of 10 pmol/µl.

2. Comparison of Linker Synthesis Efficiency

As a result of synthesizing according to the method described above, both the (1) SBP linker and the (2) LBP linker were synthesized starting from equal amounts of 5 nmol of Hybri and Biotin-loop. However, the amounts of the ultimate obtained linkers were 449.2 pmol for the (1) SBP linker and 198 pmol for the (2) LBP linker, indicating that the SBP linker was obtained at a yield nearly twice that of the LBP linker. This is thought to be due to the Hybri having favorable reactivity since the molecular weight is roughly half that of the Biotin-loop. In addition, during HPLC purification, the reaction product is thought to have adopted several two-dimensional structures due to the length of the Biotin-loop. Consequently, purification efficiency is thought to be poor in the case of the LBP linker.

(2) Comparison of Ligation Efficiency

Figure 2:
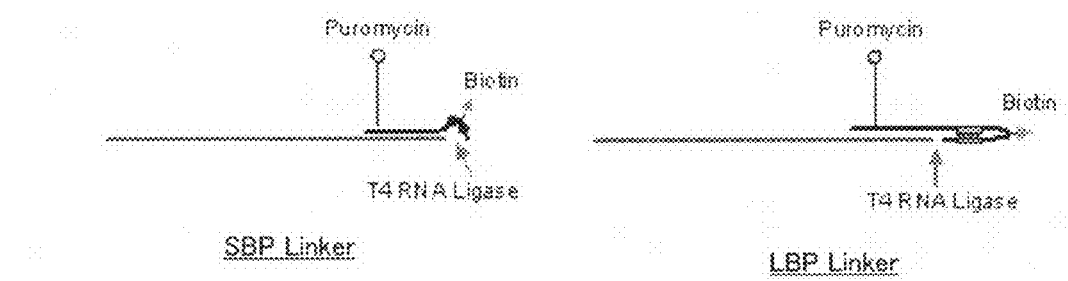
FIG. 2 is a drawing explaining ligation in the case of using an SBP linker and an LBP linker used in the examples.

The ligation efficiencies of the two types of linkers shown in FIG. 2 were compared using model mRNA consisting of the POU DNA-binding domain of Oct-1 (340 mer) and aldehyde reductase (ALR) (1.12 kmer). In FIG. 2, the arrows indicate those locations to be ligated.

1. Ligase Reaction Using T4 RNA Ligase

The ligation reaction was carried out by adding 15 pmol of linker to 10 pmol of mRNA in 20 µl of T4 RNA Ligase buffer (50 mM Tris-HCl (pH 7.5), 10 mM MgCl$_2$, 10 mM DTT, 1 mM ATP). In order to carry out annealing prior to adding the enzyme, the mixture was warmed with a heating block for 5 minutes at 70° C. followed by cooling at room temperature for 10 minutes and placing on ice. 1 µl of T4 Polynucleotide Kinase (10 U/µl, Takara), 1.5 µl of T4 RNA Ligase (40 U/µl, Takara) and 2 µl of SUPERase RNase inhibitor (20 U/µl, Ambion) were then added thereto followed by incubating for 10 to 30 minutes at 25° C.

2. Result of Ligation Reaction

The product that reacted in accordance with that described above was subjected to electrophoresis in 5% denaturing gradient acrylamide gel containing 8 M urea at 65° C. Those results are shown in FIG. 3.

Figure 3:
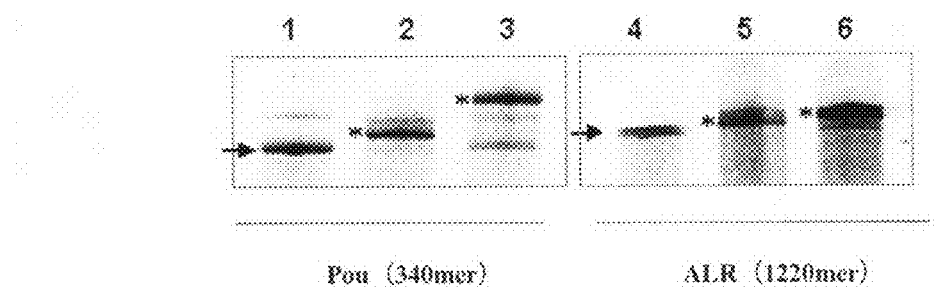
FIG. 3 is a drawing showing the results of applying a reactant obtained in the examples to denaturing gradient acrylamide gel electrophoresis.

In FIG. 3, lane 1 indicates Pou mRNA, and lane 4 indicates ALR mRNA. Lanes 2 and 5 indicate the results of carrying out the ligation reaction using the SBP linker, while lanes 3 and 6 indicate the results of carrying out the ligation reaction using the LBP linker. Furthermore, in FIG. 3, the arrows indicate the locations of mRNA or mRNA not ligated with a linker, and the asterisks (*) indicate locations ligated by a linker.

As can be understood from FIG. 3, the ligation efficiency in the case of using the SBP linker is 95% or more. On the other hand, that in the case of using the LBP linker is 80% or less, and the results remained unchanged even when the reaction time was extended to 2 hours or more. Thus, the SBP linker enabled the obtaining of a ligation efficiency equal to or greater than that of conventional linkers at a reaction time of 10 minutes, which is one-tenth the time required by conventional linkers.

(3) Cleavage Efficiency of Biotin Portion

Figure 4:
FIG. 4 is a drawing explaining cleavage of solid phase binding sites in an SBP linker and an LBP linker used in the examples.

As shown in FIG. 4, the enzymes used for cleaving the biotin portion are different between the SBP linker and the LBP linker.

1. Cleavage by RNase T1 (Case of SBP Linker)

After ligating 10 pmol of the SBP linker and the mRNA, 1 µl of SuperScript III RT reverse transcriptase (200 U/µl, Invitrogen) in 20 µl of reverse transcriptase buffer (250 mM Tris-HCl (pH 8.3), 375 mM KCl, 15 mM $MgCl_2$) was added followed by reacting for 30 minutes at 50° C. to convert to DNA. Next, RNase T1 (Ambion) was added directly thereto and allowed to react for 10 minutes at 37° C.

2. Cleavage by Restrictase PvuII (Case of LBP Linker)

After ligating 10 pmol of the LBP linker with the mRNA, 1 µl of SuperScript III RT reverse transcriptase (200 U/µl, Invitrogen) in 20 µl of reverse transcriptase buffer was added followed by reacting for 30 minutes at 50° C. to convert to DNA. 24 units of restrictase PvuII (Takara) were then added thereto and allowed to react for 2 hours at 37° C.

3. Results of Cleavage Reactions

Figure 5:
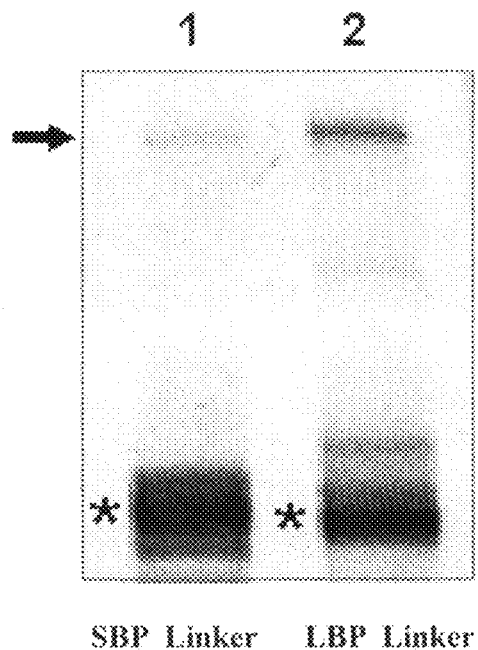
FIG. 5 is a drawing showing the results of applying a reactant following excision of a solid phase binding site to denaturing gradient acrylamide gel electrophoresis in the examples.

After carrying out the reactions described above, the results of electrophoresing the resulting reactants in acrylamide gel containing 5% 8M urea at a constant temperature of 65° C. are shown in FIG. 5. In FIG. 5, the asterisks (*) indicate bands of the decomposed products, while the arrow indicates bands of those products that were not decomposed.

As shown in FIG. 5, although nearly all of the SBP linker was decomposed, the reactant of the LBP linker was found to not be decomposed even after reacting for 2 hours.

(4) Comparison of In Vitro Virus Virion (DNA/RNA-Protein Conjugate) Synthesis Efficiency Between SBP Linker and LBP Linker The SBP linker and the LBP linker were ligated to Pou mRNA to obtain a DNA/RNA-protein conjugate in each case using the reaction scheme shown in FIG. 1. However, in the case of the LBP linker, the RNase T1 portion in the drawing was cleaved with restrictase PvuII using the method described in (3) above ("Cleavage Efficiency of Biotin Portion"). In addition, confirmation of the final product (DNA/RNA-protein conjugate) was carried out for the DNA-protein conjugate by decomposing the RNA portion using RNase H since the DNA/RNA-protein conjugate was unable to be confirmed directly by electrophoresis since the molecular weight was more than twice that of the original mRNA.

1. Ligation of mRNA to Linker DNA

Ten (10) pmol of Pou-mRNA and 15 pmol of the linker were ligated based on section "1. Ligation Reaction Using T4 RNA Ligase" of (2) above describing a comparison of the ligation reactions.

2. Purification and Precipitation of mRNA-DNA Linker

Next, the mRNA-DNA linker was purified in accordance with the protocol provided with the Qiagen RNeasy Kit to remove unligated DNA linker. The recovered mRNA-DNA linker (30 to 50 µl) was subjected to ethanol precipitation in accordance with the protocol provided with the Quick-Precip Plus solution coprecipitation agent (Edge Biosystem). The resulting precipitate was then dissolved in 4 to 10 µl of DEPC water to obtain a template for translation.

3. IVV Formation (Translation and mRNA-Protein Ligation)

All reagents used for translation were placed on ice after stirring and centrifuging. A 25 µl scale reaction was carried out by mixing in the order shown below.

0.625 µl of –methionine Master Mix and 0.625 µl of minus leucine Master Mix were mixed followed by the addition of 1.25 µl of 1 M potassium acetate. 2 µl of SUPERase RNase inhibitor (Ambion) were then added thereto. Moreover, 17 µl of Retic lysate (Ambion) were precisely added and then carefully pipetted to prevent the formation bubbles. This mixture was then added to the template prepared in 2 above. The mixture was then mixed again while being careful not to form bubbles. Next, the mixture was reacted for 20 minutes at 30° C. 3 µl of 1 M $MgCl_2$ and 7 µl of 3 M KCl were added followed by incubating for 2 hours at 37° C.

4. Immobilization of mRNA-Protein Conjugate on Streptoavidin Beads (StAV Beads)

The mRNA-protein conjugate was purified from a cell-free translation system using biotin-streptoavidin binding. With respect to the mRNA-protein conjugate formed in 3 above, first 20 µl of Magnotex-SA particles (Takara) were transferred to a 1.5 ml Eppendorf tube followed by allowing to stand undisturbed for 1 minute on a magnet stand and discarding the supernatant. Next, after washing twice with 200 µl of 1× binding buffer, a volume of 2× binding buffer equal to the volume of the mRNA-protein conjugate was added followed by addition of the washed Magnotex-SA particles thereto. The suspended particles were rotated slowly for 15 minutes at room temperature. After the binding reaction, the particles were washed twice with 10 volumes of 1× binding buffer and then washed once with 0.01% BSA solution.

5. Reverse Transcription Reaction

Stabilization of the mRNA of the immobilized mRNA-protein conjugate by converting to DNA was carried out in the manner described below.

One (1) µl of 0.1 M DTT, 1 µl of SUPERase RNase inhibitor, 3 µl of dNTP mixture (2.5 mM each) and 1 µl of SuperScript III RT (200 U/µl, Invitrogen) were added to 4 µl of 5× First-Strand Buffer (250 mM Tris-HCl (pH 8.3), 375 mM KCl, 15 mM $MgCl_2$) followed by addition of the washed beads having the mRNA-protein conjugated immobilized thereon to a final volume of 20 µl and allowing to react at 50° C. At this time, the tube was rotated to ensure that the beads did not settle.

6. Excision of DNA/RNA-Protein Conjugate from StAV Beads

Cleavage reactions were respectively carried out for the SBP linker and the LBP linker according to the method described in (3) above "Cleavage Efficiency of Biotin Portion". Following completion of the reaction time, the beads were adsorbed to the wall using a magnet stand, and the supernatant containing the excised DNA/RNA-protein conjugate was recovered.

7. Decomposition Reaction of RNA Portion by RNase H

Figure 6:
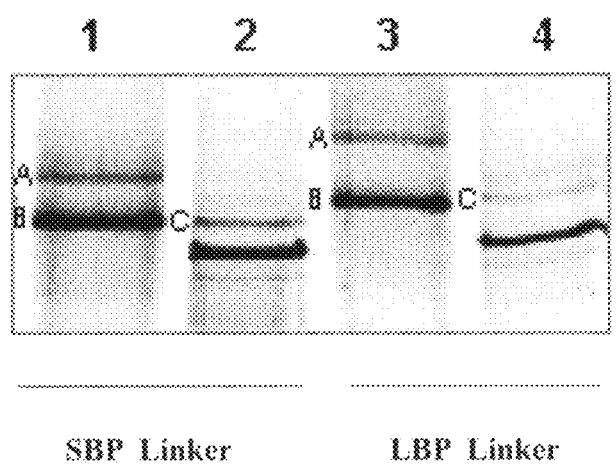
FIG. 6 is a drawing showing the results of applying a reaction product following RNase H treatment to denaturing gradient acrylamide gel electrophoresis in the examples.

One (1) μl of RNase H (Ambion) was added to the supernatant obtained in 6 above and reacted for 20 minutes at 40° C. The reactants were analyzed by SDS-PAGE using 8 M urea in 6% acrylamide gel. Those results are shown in FIG. 6. In FIG. 6, lanes 1 and 2 indicate the results of the IVV reaction for the SBP linker, while lanes 3 and 4 indicate the results of the IVV reaction for the LBP linker. In lanes 1 and 3, "A" indicates the locations of the mRNA-protein conjugate, while "B" indicates the locations of the mRNA and linker conjugate. In lanes 2 and 4, "C" indicates the locations of the cDNA-protein conjugate.

As can be understood from the results of FIG. 6, although the amounts of mRNA ligated to the SBP linker and the LBP linker are equal, a comparison of lanes 1 and 3 reveals that the band of lane 1 is darker overall (namely, indicates a larger amount). This is because of the shorter ligation reaction time with the linker and better efficiency of the SBP linker, which is thought to result in less decomposition of the RNA. In addition, a comparison of lanes 2 and 4 reveals that the band of the cDNA-protein conjugate at the location of C is nearly twice as dark for the SBP linker as compared with the LBP linker. This means that the amount of the final DNA/RNA-protein conjugate obtained with the SBP linker was twice that of the LBP linker. Since the SBP linker is able to be completely excised in a shorter period of time than the LBP linker, and the entire process can be carried out in less than half the time, there is less decomposition of RNA, thereby resulting in the final yield being more than twice that than in the case of the LBP linker. Moreover, since the synthesis cost of the linker itself can be reduced to less than half, it is believed that at least a four-fold improvement in efficiency can be achieved overall as compared with the prior art.

INDUSTRIAL APPLICABILITY

According to the present invention, a linker for constructing an mRNA-puromycin-protein conjugate is provided that has satisfactory synthesis efficiency and can be produced inexpensively. In addition, a linker in a preferable aspect of the present invention can be designed shorter than a conventional linker while also offering the advantages of having satisfactory ligation efficiency with mRNA and being able to be purified rapidly and efficiently. As a result, the present invention leads to promotion of the application of in vitro virus technology, and lead to expectations for advances in evolutionary molecular engineering aimed at analyzing the functions of DNA and proteins and acquiring functional proteins.

The invention claimed is:

1. A linker for ligating mRNA and puromycin or a puromycin-like compound to construct an mRNA-puromycin conjugate, an mRNA-puromycin-protein conjugate or an mRNA/cDNA-puromycin-protein conjugate, the linker comprising the nucleic acid sequence of SEQ ID NO:1 as a main backbone, wherein a solid phase binding site consisting of biotin-deoxythymine is at position 5, a pair of cleavage sites consisting of Ribo-guanosines and cleavable by an enzyme are at positions 3 and 7, and a puromycin or puromycin-like compound conjugating site consisting of amino-modified deoxythymine is at position 23, and wherein the enzyme is selected from the group consisting of RNase T1, RNase A, RNase I and pancreatic RNase.

2. The linker according to claim 1, wherein the enzyme is RNase T1, RNase A or RNase I.

3. An mRNA-puromycin conjugate in which mRNA and puromycin or a puromycin-like compound are ligated with the linker according to claim 1.

4. An immobilized mRNA-puromycin conjugate in which an mRNA-puromycin-protein conjugate in which mRNA and puromycin or puromycin-like compound is bound to a solid phase through a solid phase binding site provided in the linker according to claim 1.

5. The immobilized mRNA-puromycin conjugate according to claim 4, wherein the solid phase is selected from the group consisting of styrene beads, glass beads, agarose beads, sepharose beads, magnetic beads, glass plate, silicon plate, plastic plate, metal plate, glass container, plastic container and membrane.

* * * * *

UNITED STATES PATENT AND TRADEMARK OFFICE
CERTIFICATE OF CORRECTION

| | |
|---|---|
| PATENT NO. | : 8,445,413 B2 |
| APPLICATION NO. | : 11/665300 |
| DATED | : May 21, 2013 |
| INVENTOR(S) | : Naoto Nemoto and Manish Biyani |

It is certified that error appears in the above-identified patent and that said Letters Patent is hereby corrected as shown below:

On the Title page, item (75) Inventors:, the first inventor's name "Naota" should be --Naoto--.

Signed and Sealed this
Twenty-seventh Day of August, 2013

Teresa Stanek Rea
*Acting Director of the United States Patent and Trademark Office*

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: Ribo-G
<220> FEATURE:
<221> NAME/KEY: modified_base
<222> LOCATION: (5)
<223> OTHER INFORMATION: Biotin-dT
<220> FEATURE:
<221> NAME/KEY: modified_base
<222> LOCATION: (7)
<223> OTHER INFORMATION: Ribo-G
<220> FEATURE:
<221> NAME/KEY: modified_base
<222> LOCATION: (23)
<223> OTHER INFORMATION: Amino-Modifier C6 dT

<400> SEQUENCE: 1
ccncncnccc cgccgccccc cgncct                                          26

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)
<223> OTHER INFORMATION: Biotin-dT
<220> FEATURE:
<221> NAME/KEY: modified_base
```

```
<222> LOCATION: (53)
<223> OTHER INFORMATION: Amino-Modifier C6 dT

<400> SEQUENCE: 2
cccggtgcag ctgtttcatc ncggaaacag ctgcaccccc cgccgccccc cgncct        56
```